(12) United States Patent
Liu et al.

(10) Patent No.: US 8,524,492 B2
(45) Date of Patent: Sep. 3, 2013

(54) CULTURE METHOD FOR AMPLIFYING LARGE NUMBERS OF HAIR FOLLICLE STEM CELLS IN VITRO

(75) Inventors: Jinyu Liu, Changchun (CN); Yulin Li, Changchun (CN)

(73) Assignee: Jilin University (CN)

( * ) Notice: Subject to any disclaimer, the term of this patent is extended or adjusted under 35 U.S.C. 154(b) by 0 days.

(21) Appl. No.: 13/517,068

(22) PCT Filed: Jul. 20, 2011

(86) PCT No.: PCT/CN2011/001185
§ 371 (c)(1),
(2), (4) Date: Jun. 19, 2012

(87) PCT Pub. No.: WO2012/009958
PCT Pub. Date: Jan. 26, 2012

(65) Prior Publication Data
US 2012/0252121 A1    Oct. 4, 2012

(30) Foreign Application Priority Data
Jul. 22, 2010  (CN) .......................... 2010 1 0238 350

(51) Int. Cl.
*C12N 5/00* (2006.01)

(52) U.S. Cl.
USPC ............................ 435/325; 435/375; 435/383

(58) Field of Classification Search
USPC .......................................... 435/325, 378, 383
See application file for complete search history.

(56) References Cited

U.S. PATENT DOCUMENTS
7,655,465 B2 *    2/2010   Sherley et al. ................ 435/377

* cited by examiner

*Primary Examiner* — Karen Cochrane Carlson
*Assistant Examiner* — Natalie Moss
(74) *Attorney, Agent, or Firm* — Banner & Witcoff, Ltd.

(57) ABSTRACT

The present invention is a method for amplifying a large numbers of hair follicle stem cells in vitro by using microspheres as carriers for cell culture and a revolving bottle as a fermentation tank for cell proliferation. The method includes digesting hair follicles to obtain hair follicle stem cells, seeding the cells on microcarriers, transferring the microcarriers to a revolving bottle, feeding liquid culture media into the revolving bottle, placing the revolving bottle into a cell incubator, growing the cells on the microcarrier and harvesting the hair follicle stem cells.

10 Claims, 3 Drawing Sheets

CULTURE METHOD FOR AMPLIFYING LARGE NUMBERS OF HAIR FOLLICLE STEM CELLS IN VITRO

RELATED APPLICATION DATA

This application is a National Stage Application under 35 U.S.C. 371 of co-pending PCT application PCT/CN2011/001185 designating the U.S. and filed Jul. 20, 2011; which claims the benefit of CN patent application number 201010238350.3 and filed Jul. 22, 2010 each of which are hereby incorporated by reference in their entireties.

FIELD OF TECHNOLOGY

The present invention belongs to the field of cell culture technology, specifically related to a culture method for in vitro mass production of adherent cells in large scale, particularly the bioreactor technology for in vitro mass production of hair follicle-derived stem cells in large scale, using microspheres as carriers for cell culture and spinning bottles as ferment tanks.

BACKGROUND

Diseases pose a significant threat to the health and survival of human race, which are the most important social issues for countries around the world. The advent and progress of stem cell transplantation have brought opportunity and hope to the patients who have been considered to be "incurable" by traditional treatment. While the sources of stem cells together with the safety and efficacy of transplantation therapy have always been the major scientific issues that the need to be addressed in cell based regenerative medicine Hair follicle is one of the appendages of skin, originated in the interaction of epidermis and mesenchyme during embryonic development. In addition to keratinocyte stem cells and melonocyte stem cells, hair follicle also contains mesenchymal stem cells. The mesenchymal stem cells in hair follicle can not only self-renew, but also differentiate into bones, cartilage, fat and vascular smooth muscle and other tissue-specific cells. The self-renewal and differentiation of hair follicle stem cells have laid the cytological basis for the research and application of regenerative medicine of a variety of tissues and organs, including hair follicles. With advantages of easily accessible rich source of autologous stem cells, hair follicle stem cells exhibit the most clinical application potential over other adult stem cells currently known. However, the initiation of cell therapy needs large amount of highly proliferative stem cells, which can be achieved by repeated subculture of the anchorage dependent cells, such as hair follicle derived stem cells, in flasks or tissue culture petridishes. This process for harvesting of anchorage dependent cells not only reduce the proliferative capacity of the cells, but also deprive the cells of their potential to differentiate into a variety of tissue-specific cells, which may even induce the formation of tumor after transplant. As it is known that the amount of adherent cells harvested is proportional to culture area, namely: the larger the culture surface area is, the more amount of anchorage dependent cells harvest. Microcarrier has a high ratio of area to volume. The surface area of 1 kilogram of microcarriers with diameter of 100-300 microns, such as Cultisphere-G, is about 1 square meter. Thus with the use of microcarriers for cell culture surfaces, a large amount of adherent cells can be produced in a small amount of media, which can satisfy the number of cells required for cell based regeneration, avoid the reduction of cell proliferation capacity and the decline in differentiation potential as well as the risk of inducing tumor formation after transplantation, and also reduce the production costs. Therefore, the microcarrier cell culture system has been widely used in biological research and clinical application, and have achieved satisfactory results.

DESCRIPTION OF THE INVENTION

The purpose of this invention relates to a method for rapid in vitro amplification of a large number of hair follicle stem cells that can be used as seed cells for the therapy, treatment and repair of diseased tissues and organs.

The "revolving bottle for cell culture" mentioned in the present invention refers to containers for cell culture, such as: but not limited to, vertical revolving bottles and horizontal revolving bottles. The volume is 10-10000 ml, and the spinning speed during culture is set to be 1-500 RPM;

The "microcarrier" mentioned in the present invention is the media for cell culture that consist of one or several kinds of biodegradable materials, or non-biodegradable materials, or biodegradable and non-biodegradable materials, with the shape of, such as: but not limited to, particles, films and lumps. The microcarrier of the present invention are preferably spherical or ellipsoidal particles, whose average size range is usually from 10 μm to 1000 μm, preferably from 20 μm to 800 μm, and more preferably from 100 μm to 300 μm, from 301 μm to 500 μm and from 501 μm to 800 μm, such as: but not limited to 100 μm, 150 μm, 200 μm, 250 μm, 300 μm, 350 μm, 400 μm, 450 μm, 500 μm, 550 μm, 600 μm, 650 μm, 700 μm, 750 μm and 800 μm.

The "biodegradable materials" mentioned in the present invention refers to the polymer materials that can be degraded or decomposed through the organism's own biological or biochemical processes, such as: but not limited to, collagen, blood fibrinolytic protein, gelatin, hyaluronic acid, polylactic acid, poly glycolic acid, polyurethane and chitosan.

The "non-biodegradable materials" of the present invention refers to glass, silicone, metal and plastics.

The "cells" of the present invention are hair follicle stem cells taken from human, wildlife and livestock, gained in vivo or isolated in vitro through a variety of methods. Wild animals are undomesticated animals in natural state. Livestock means animals bred by man to provide food, such as: but not limited to, dogs, rats, hamsters, pigs, horses, rabbits, cows, buffalo, bull, sheep, goats, geese and chickens and so on. The "cells" used are preferably from mammals, especially hair follicle stem cells of human.

The "media" of the present invention takes one of DMEM (Dulbecco's Modified Eagle Media), DMM-F12, EGM (Endothelial Growth Media), KGM (Keratinocyte Growth Media), IMDM (Iscove's Modified Dulbecco's Media), MEM(Minimum Essential Media) and EBM (Eagle's Basal Media) as the basal media, and contains a mixture of one or more biological factors.

The "biological factor" of the present invention refers to the group consisting of Insulin-like Growth Factor (IGF), basic Fibroblast Growth Factors (bFGF), Epidermal Growth Factor (EGF), Vascular Endothelial Growth Factor (VEGF), phosphate vitamin C, dexamethasone, insulin, transferrin, animal pituitary extract, penicillin-streptomycin, amphotericin, and serum from human or animals.

The above biological factor should be used in moderate amount to help promote cell proliferation, and the proper amount of each of the above cytokines ranges from 0.1 ng/ml to 500 ng/ml, preferably from 0.5 ng/ml to 100 ng/ml, further to be from 1 ng/ml to 20 ng/ml, from 21 ng/ml to 40 ng/ml, from 41 ng/ml to 80 ng/ml and from 81 ng/ml to 100 ng/ml, such as; but not limited to positive integer concentration range of 1-100 (ng/ml).

The "animal serum" mentioned in the present invention is selected from one or several kinds of mammal serum, such as bovine serum, sheep serum and pig serum. The "animal serum" should be added in proper amount as biological factor so as to help promote cell proliferation, the proper amount range of which shall be 0.1-30% of the overall volume of media, preferably 1-25%, further to be 1-5%, 6-10%, 11-15% and 16-20%, such as: but not limited to: 1%, 2%, 3%, 4%, 5%, 6%, 7%, 8%, 9%, 10%, 11%, 12%, 13%, 14%, 15%, 16%, 17%, 18%, 19% and 20%.

The methods to culture hair follicle stem cells provided in the present invention include:
(1) digesting hair follicles or hair follicle tissue blocks in the presence of protease to obtain the cells, seeding the cells, to microcarriers, with a density range from $1\times10^3$ cells/g microcarrier to $1\times10^8$ cells/g microcarrier, and then suspending them in the liquid culture media. The density of cells seeded should preferably be from $2.5\times10^6$ to $2\times10^7$ cells/g, especially from $2.5\times10^6$ to $1\times10^7$ cells/g, such as: but not limited to, $2.5\times10^6$ cells/g, $3\times10^6$ cells/g, $4\times10^6$ cells/g, $5\times10^6$ cells/g, $6\times10^6$ cells/g, $7\times10^6$ cells/g, $8\times10^6$ cells/g, $9\times10^6$ cells/g, $1\times10^7$ cells/g.
(2) transfering the microcarriers, together with the cells on them, into a revolving bottle for cell culture.
(3) according to the volume of the said revolving bottle, feeding the said liquid culture media into the revolving bottle to 1/10-1/3 of the volume.
(4) placing the revolving bottle into cell incubator for cell culture. Under the conditions of 37° C., 5v/v % $CO_2$, the revolving bottle rotates 1-5 minutes every hour, and the rotation speed is 10-300 rounds/min.
(5) using digestive agent to digest the said cells from the said microcarriers, when cells have nearly grown into a monolayer on the microcarriers, and then using 0.25% trypsin −0.02% EDTA solution to digest the cells from the microcarriers, inactivate trypsin with serum, and then wash away serum and antibiotics with phosphate buffer solution, and finally get an amplified number of hair follicle stem cells.

The method of obtaining hair follicle stem cells by digesting hair follicles with protease in the present invention should be comprehended as obtaining individual hair follicle stem cells by digesting hair follicles with protease, for example, wash hair follicles or hair follicle tissue blocks with phosphate buffered solution (PBS), then use 0.25% trypsin −0.02% EDTA solution at 37° C. to digest for 3-30 minutes, inoculate the cells to orifice plate when fetal bovine serum is terminated. Technicians in the field can see, any way to obtain individual cells by digesting hair follicles with protease should be applicable to the present invention. The method of obtaining hair follicle stem cells from tissue blocks adopted in the present invention should be comprehended as removing hair follicle stem cells from hair follicles by the way of culture. The specific steps, reagents and conditions involved in the present invention to culture hair follicles are listed for the need of full disclosure, which shall not limit the invention.

The present invention is a method, belonging to the field of cell culture, for amplifying a large numbers of hair follicle stem cells in vitro by using microspheres as carriers for cell culture and a revolving bottle as a fermentation tank for cell proliferation. The method is simple in its procedures, is economical and practical, and avoids side effects associated with the traditional cell amplification method, such as the weakening of cell proliferation capability, the reduction of differentiation potential and the like caused by repeated cell subculture, and also reduces the consumption of the culture solution; the hair follicle stem cells amplified by the method can still keep the original proliferation capability and differentiation potential, and can be used for: (1) establishing hair follicle stem cell bank to provide high-quality seed cells for related research on adult stem cells; (2) transplanting and repairing tissues and organs subjected to pathological changes; (3) constructing tissue-engineered organs to be used as substitute autologous organs for transplantation or repair of organs subjected to pathological changes or missing organs; and (4) serving as target cells for the genetic treatment of corresponding diseases.

The hair follicle stem cells obtained by the present invention can serve as cells seeding after being released from microcarriers through protease digestion. They can be used to carry out cell therapy, cure diseased tissues and organs, construct tissue engineering organs for transplantation of diseased or deficient organs, or be used as target cells in gene therapy for transplantation and treatment of metabolic or congenital disorders. The degradable microcarriers, together with their hair follicle stem cells, can be directly transplanted into diseased area to treat corresponding diseased tissues and organs or to improve the status of the corresponding diseased organs, enhance their functionality, so as to achieve the purpose of the repair of tissues and organs.

EXAMPLES

The following passages describe the technical solution of the invention in detail with attached figures. The examples of the invention only illustrate the technical solution of the present invention rather than set limits. Despite the present invention is described in detail with the reference to preferred embodiments, ordinary technicians in the field should understand that the technical solution of the invention can be modified or replaced with equivalents, which will not deviate from the spirit and scope of the technical solution of the present invention and shall be covered by the requirements of the claim of rights in this invention.

Unless explicitly specified, all reagents used in this invention shall be purchased from Sigma-Aldrich.

Example 1

Preparation of Instrument and Materials
(1) Revolving bottle for cell culture: CELLSPIN (purchased from IBS), the volume is 500 ml and the spinning speed is 20 RMP;
(2) Carriers: microspheres made of gelatin with an average size of 200 μm;
(3) Media: basal media is DMEM (purchased from Invitrogen), to which added a proper amount of epidermal growth factor (EGF);

The Culture and Amplification of Hair Follicle Stem Cells:
(1) Human hair follicle stem cells are obtained by digesting hair follicles or hair follicle tissue blocks with protease, specifically, wash hair follicles or hair follicle tissue blocks with phosphate buffered solution (PBS), then use 0.25% trypsin –0.02% EDTA solution at 37° C. to digest for 10 minutes, inoculate the cells to orifice plate when fetal bovine serum is terminated, then inoculate them to microcarriers with a density of $1\times10^3$-$1\times10^7$ cells/g, and suspend them in culture media.
(2) transfering the microcarriers, together with the cells on them, to the revolving bottle.
(3) adding media to ⅕ of the container according to the volume of the revolving bottle.
(4) placing the revolving bottle into cell incubator for cell culture. The condition of culture is 37° C., 5v/v % CO2. The revolving bottle shall rotate 1-5 minutes every hour with a speed of 10-300 RPM.
(5) When the cells have nearly grown to a monolayer on the microcarriers, use 0.25% trypsin –0.02% EDTA solution to digest the cells from the microcarriers, inactivate trypsin with serum, and then wash away serum and antibiotics with phosphate buffer solution, finally we get amplified number of hair follicle stem cells.

Figure 1:
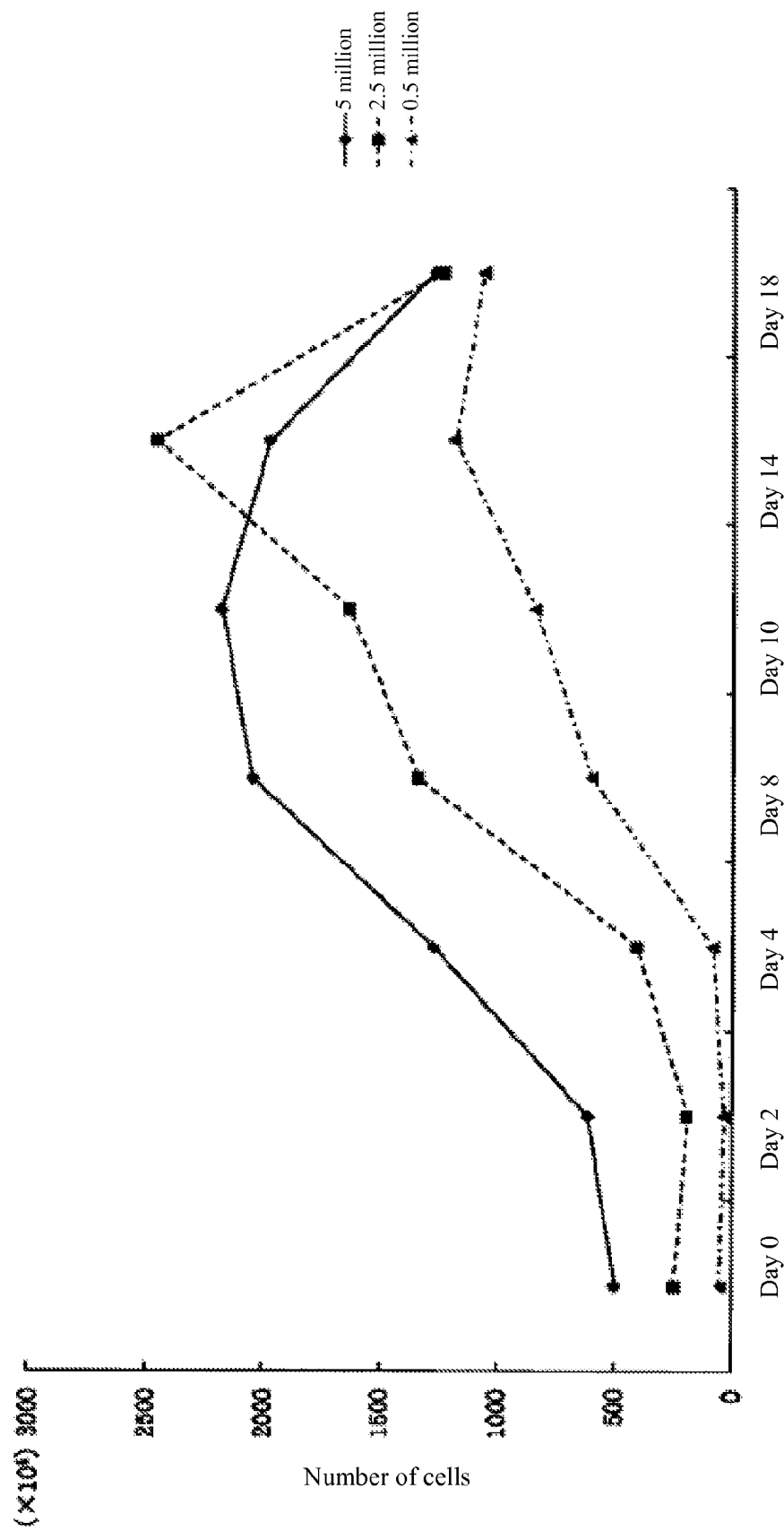
FIG. 1 shows the curve of cell growth on the carriers, in which the legend "5 million", "2.5 million" and "0.5 million" mean the initial numbers of cells inoculated on microcarriers of 0.5 g.

The hair follicle stem cells are respectively seeded onto the 0.5 g above mentioned gelatin microcarriers in the number of "0.5 million", "2.5 million" and "5 million". The growth curve of cells is shown in FIG. 1: in 2-14 days after seeding, the cells enter into the exponential phase of growth, the number of which is rapidly amplified. Among the above three curves, "5 million per gram microcarriers" is a preferred initial number of cells for seeding.

Example 2

Preparation of Instrument and Materials
(1) Revolving bottle for cell culture: CELLSPIN (purchased from IBS), the volume is 500 ml and the spinning speed is 20 RMP;
(2) Carriers: microspheres made of gelatin with an average size of 200 μm;
(3) Media: basal media is DMEM (purchased from Invitrogen), to which added 5 ng/ml of epidermal growth factor (EGF);

The Culture and Amplification of Hair Follicle Stem Cells:
(1) human hair follicle stem cells are obtained by digesting hair follicles or hair follicle tissue blocks with protease, specifically, wash hair follicles or hair follicle tissue blocks with phosphate buffered saline (PBS), then use 0.25% trypsin –0.02% EDTA solution at 37° C. to digest for 10 minutes, inoculate the cells to orifice plate when fetal bovine serum is terminated, then inoculate them to microcarriers with a density of $5\times10^6$ cells/g, and suspend them in culture media.
(2) transfering the microcarriers, together with the cells on them, to the revolving bottle.
(3) adding media to ⅕ of the container according to the volume of the revolving bottle.
(4) placing the revolving bottle into cell incubator for cell culture. The condition of culture is 37° C., 5v/v % CO2. The revolving bottle shall rotate 1-5 minutes every hour with a speed of 10-300 RPM.
(5) When the cells have nearly grown to a monolayer on the microcarriers, use 0.25% trypsin –0.02% EDTA solution to digest the cells from the microcarriers, inactivate trypsin with serum, and then wash away serum and antibiotics with phosphate buffer solution, finally we get amplified number of hair follicle stem cells.

Figure 2:
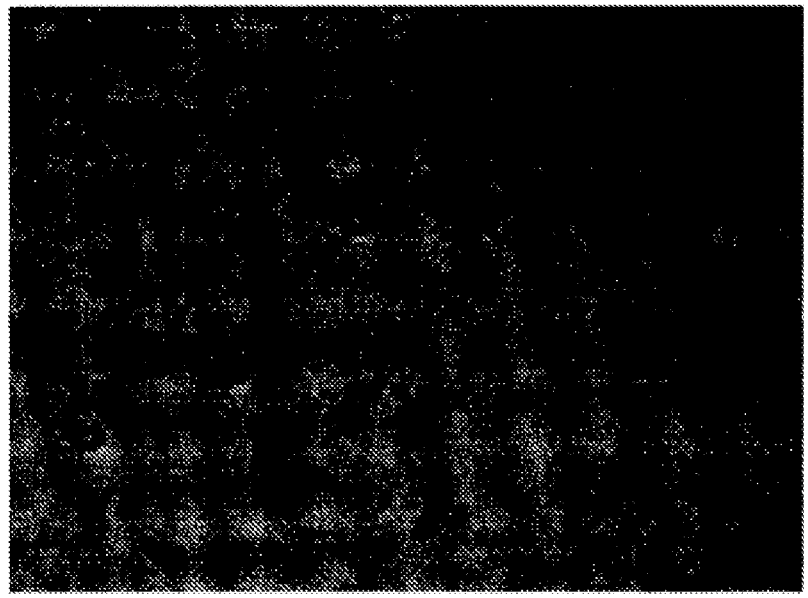
FIG. 2 shows the results of hair follicle stem cells obtained by the amplification method of the present invention after being treated by the way of regular adipogenic cells in vitro induced differentiation and oil red O staining The adipogenic cells stained by oil red O are shown as the arrows in this figure.

Treat the hair follicle stem cells obtained by the amplification method of the present invention by the way of regular adipogenic cells in vitro induced differentiation and oil red O staining. The experiment proved that the hair follicle stem cells obtained by the amplification have successfully differentiated into adipogenic cells (FIG. 2), thus have differentiation potential:

Example 3

Preparation of Instrument and Materials
(1) Revolving bottle for cell culture: CELLSPIN (purchased from IBS), the volume is 500 ml and the spinning speed is 20 RMP;
(2) Carriers: microspheres made of gelatin with an average size of 200 μm;
(3) Media: basal media is DMEM (purchased from Invitrogen), to which added 10 ng/ml of bFGF and 5 ng/ml of epidermal growth factor (EGF);

The Culture and Amplification of Hair Follicle Stem Cells:
(1) Human hair follicle stem cells are obtained by digesting hair follicles or hair follicle tissue blocks with protease, specifically, wash hair follicles or hair follicle tissue blocks with phosphate buffered solution (PBS), then use 0.25% trypsin –0.02% EDTA solution at 37° C. to digest for 10 minutes, inoculate the cells to orifice plate when fetal bovine serum is terminated, then inoculate them to microcarriers with a density of $1\times10^7$ cells/g, and suspend them in culture media.
(2) transfering the microcarriers, together with the cells on them, to the revolving bottle.
(3) adding media to ⅕ of the container according to the volume of the revolving bottle.
(4) placing the revolving bottle into cell incubator for cell culture. The condition of culture is 37° C., 5v/v % $CO_2$. The revolving bottle shall rotate 1-5 minutes every hour with a speed of 10-300 RPM.
(5) When the cells have nearly grown to a monolayer on the microcarriers, use 0.25 trypsin –0.02% EDTA solution to digest the cells from the microcarriers, inactivate trypsin with serum, and then wash away serum and antibiotics with phosphate buffer solution, finally we get amplified number of hair follicle stem cells.

Figure 3:
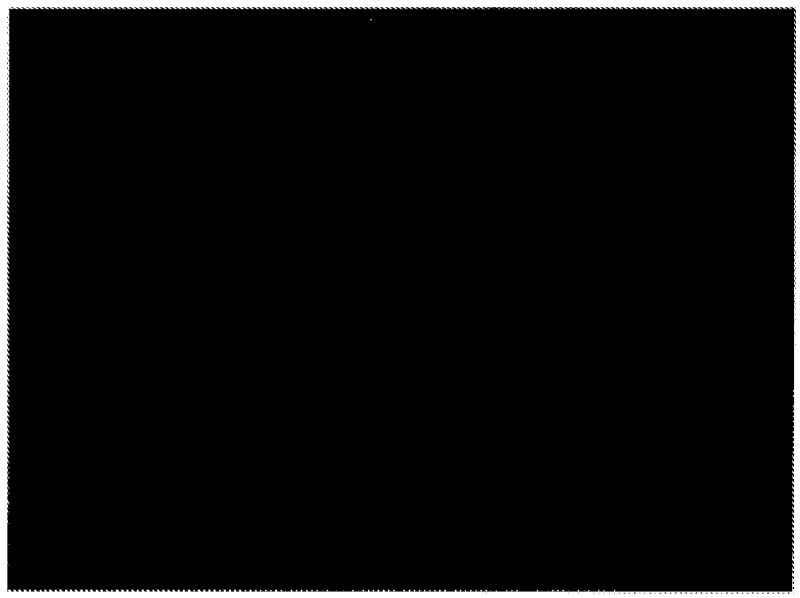
FIG. 3 shows the results of hair follicle stem cells obtained by the amplification method of the present invention after being treated by the way of regular osteoplasts in vitro induced differentiation and alizarin red staining. The osteoplasts stained by alizarin red are shown as the arrows in this figure.

Treat the hair follicle stem cells obtained by the amplification method of the present invention by the way of regular osteoplasts in vitro induced differentiation and alizarin red staining The experiment proved that the hair follicle stem cells obtained by the amplification have successfully differentiated into osteoplasts (see FIG. 3), thus have differentiation potential:

Example 4

Preparation of Instrument and Materials
(1) Revolving bottle for cell culture: CELLSPIN (purchased from IBS), the volume is 500 ml and the spinning speed is 20 RMP;
(2) Carriers: microspheres made of gelatin with an average size of 200 μm;
(3) Media: basal media is DMEM (purchased from Invitrogen), to which added 10 ng/ml of bFGF, 10% (v/v) of fetal bovine serum and 10 ng/ml of epidermal growth factor (EGF);

The Culture and Amplification of Hair Follicle Stem Sells:
(1) human hair follicle stem cells are obtained by digesting hair follicles or hair follicle tissue blocks with protease, specifically, wash hair follicles or hair follicle tissue blocks with phosphate buffered saline (PBS), then use 0.25% trypsin –0.02% EDTA solution at 37° C. to digest for 10 minutes, inoculate the cells to orifice plate when fetal bovine serum is terminated, then inoculate them to microcarriers with a density of $1\times10^7$ cells/g, and suspend them in culture media.
(2) transfering the microcarriers, together with the cells on them, to the revolving bottle.
(3) adding media to ⅓ of the container according to the volume of the revolving bottle.
(4) placing the revolving bottle into cell incubator for cell culture. The condition of culture is 37° C., 5v/v % CO2. The revolving bottle shall rotate 1-5 minutes every hour with a speed of 10-300 RPM.
(5) When the cells have nearly grown to a monolayer on the microcarriers, use 0.25 trypsin –0.02% EDTA solution to digest the cells from the microcarriers, inactivate trypsin with serum, and then wash away serum and antibiotics with phosphate buffer solution, finally we get amplified number of hair follicle stem cells.

Figure 4:
FIG. 4 shows the results of hair follicle stem cells obtained by the amplification method of the present invention after being treated by the way of regular chondroblast in vitro induced differentiation and alcian blue staining. The chondroblasts stained by alcian blue are shown as the arrows in this figure.

Treat the hair follicle stem cells obtained by the amplification method of the present invention by the way of regular chondroblasts in vitro induced differentiation (Tissue Eng 2001,7,211-28) and alcian blue staining. The experiment proved that the hair follicle stem cells obtained by the amplification have successfully differentiated into chondroblasts (FIG. 4), thus have differentiation potential:

The invention claimed is:

1. A method for amplifying large numbers of hair follicle stem cells in vitro, comprising the following steps :
   (1) digesting hair follicles or a hair follicle tissue block in the presence of protease to obtain the cells, seeding the said cells on microcarriers with a density range from $1\times10^3$ cells per gram of microcarrier to $1\times10^8$ cells per gram of microcarrier, and then suspending the microcarriers in liquid culture media;
   (2) transfering the said microcarriers, together with the cells, into a revolving bottle;
   (3) feeding liquid culture media into the said revolving bottle to 1/10-⅓ of it's volume;
   (4) placing the said revolving bottle into a cell incubator for cell culture, under the conditions of 37° C., 5v/v%$CO_2$, and rotating the said revolving bottle 1-5 minutes every hour, and the rotation speed is 10-300 rounds/min;
   (5) using a digestive agent to digest the said cells from the said microcarriers, when the said cells have nearly grown to a monolayer on the microcarriers, and then, inactivating the said digestive agent by using serum, and after washing away serum and antibiotics by using phosphate buffer solution, harvesting the amplified hair follicle stem cells.

2. The method of claim 1, wherein the said digestive agent is a solution including 0.25% trypsin and 0.02% EDTA.

3. The method of claim 1, wherein the said liquid culture media is DMEM, DMM-F12, EGM, KGM, IMDM, MEM or EBM as basal media, and contains a mixture of one or more biological factors.

4. The method of claim 3, wherein the said one or more biological factors is IGF, bFGF, EGF, VEGF, Phosphate vitamin C, dexamethasone, insulin, transferrin, animal pituitary extract, penicillin-streptomycin, amphotericin, human serum or animal serum.

5. The method of claim 4, wherein the said animal serum is bovine serum, sheep serum or pig serum.

6. The method of claim 1, wherein the said microcarriers include biodegradable materials or non-biodegradable materials.

7. The method of claim 6, wherein the said biodegradable materials include collagen, blood fibrinolytic protein, gelatin, hyaluronic acid, polylactic acid, poly glycolic acid, polyurethane or chitosan.

8. The method of claim 6, wherein the said non-biodegradable materials include glass, silicone, metal or plastics.

9. The method of claim 1, wherein the said microcarriers are spherical or ellipsoidal particles, with an average particle size range from 10μm to 1000μm.

10. The method of claim 1, wherein the said microcarriers are spherical or ellipsoidal particles, with an average particle size range from 100μm to 800μm.

\* \* \* \* \*